(12) United States Patent
Jadwizak et al.

(10) Patent No.: US 8,755,908 B2
(45) Date of Patent: Jun. 17, 2014

(54) CONDUCTIVE COIL ARRANGEMENT AND ELECTRODE CATHETER ARRANGEMENT, IN PARTICULAR FOR CARDIAC THERAPY

(71) Applicant: BIOTRONIK SE & Co. KG, Berlin (DE)

(72) Inventors: Detmar Jadwizak, Erkner (DE); Jochen Palm, Mahlow (DE); Pierre Weitzig, Berlin (DE); Carsten Fruendt, Berlin (DE); Gordon Hillebrand, Berlin (DE); Thomas Guenther, Michendorf (DE); Carsten Steglich, Berlin (DE); Jan Helge Richter, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 13/711,007

(22) Filed: Dec. 11, 2012

(65) Prior Publication Data

US 2013/0150941 A1    Jun. 13, 2013

Related U.S. Application Data

(60) Provisional application No. 61/569,797, filed on Dec. 13, 2011.

(51) Int. Cl.
*A61N 1/00* (2006.01)
(52) U.S. Cl.
USPC .......................................................... 607/122
(58) Field of Classification Search
USPC .................... 607/122, 128; 29/885
See application file for complete search history.

(56) References Cited

U.S. PATENT DOCUMENTS

| 5,845,396 | A | * | 12/1998 | Altman et al. | ............ 29/885 |
| 2002/0099430 | A1 | | 7/2002 | Verness | |
| 2002/0151949 | A1 | | 10/2002 | Dahl et al. | |
| 2007/0038280 | A1 | * | 2/2007 | Bodner et al. | ............ 607/128 |
| 2008/0039896 | A1 | | 2/2008 | Osypka | |
| 2012/0053668 | A1 | | 3/2012 | Weitzig et al. | |

FOREIGN PATENT DOCUMENTS

DE    3304506 A1    8/1984

OTHER PUBLICATIONS

European Search Report and Notes to the European Search Report on European Patent Application No. EP 12 19 0717, dated Mar. 18, 2014 (6 pages).

* cited by examiner

*Primary Examiner* — Robert N Wieland
(74) *Attorney, Agent, or Firm* — Buchanan Ingersoll & Rooney PC

(57) ABSTRACT

A conductive coil arrangement, in particular for electrode catheters for cardiac therapy, including a multipolar conductive coil having a plurality of coradially interwoven individual coil wires and a contact zone in which at least one individual coil wire from the conductive coil can be connected to a contact element for electrical contacting. The at least one individual coil wire to be contacted is routed outwardly out of the wire interconnection of the conductive coil with a radial direction component. The remainder of the conductive coil is routed further centrally axially through the contact zone.

13 Claims, 11 Drawing Sheets

CONDUCTIVE COIL ARRANGEMENT AND ELECTRODE CATHETER ARRANGEMENT, IN PARTICULAR FOR CARDIAC THERAPY

CROSS-REFERENCE TO RELATED APPLICATIONS

This patent application claims the benefit of co-pending U.S. Provisional Patent Application No. 61/569,797, filed on Dec. 13, 2011, which is hereby incorporated by reference in its entirety.

TECHNICAL FIELD

The present invention relates to a conductive coil arrangement, in particular for electrode catheters for cardiac therapy, comprising a multipolar conductive coil having a plurality of coradially interwoven individual coil wires, and a contact zone in which at least one individual coil wire from the conductive coil can be connected to a contact element for electrical contacting. The present invention furthermore relates to an electrode catheter device in which such a conductive coil arrangement is used.

BACKGROUND

Regarding the background of the invention, it should be noted that a complex, rigid mechanism has been used over a long distance, as is known, to electrically and mechanically connect the individual coil wires of coradial, multipolar conductive coils. An example thereof is a connection of individual coil wires to a ring electrode of an electrode catheter, as shown in an older application published under U.S. Publication No. 2012/0053668, with simultaneous passage of a single coil wire through said ring electrode.

Furthermore, electrode supply leads having a so-called multiple-lumen design are known, wherein the supply leads are designed as so-called cords. They are connected to a multipolar plug, such as the type used by the Applicant herein, as known, having the name "DF-4". The electrode catheters are based on a multiple-lumen tube which guides electrically conductive cords or coils from the top electrodes and ring electrodes to the connecting plug in a plurality of axes extending parallel to the longitudinal axis of the tube. The contact ends of the cords or coils, which extend toward one another, and the contact elements in the plug have an axial orientation with respect to one another, and are therefore relatively easily accessible for a related electrical connection.

The connection of conductive coils to components to be contacted has previously been carried out preferably by placing the particular coil end or individual wires on shoulders or projections of contact sleeves, wherein the electrical connection is achieved by way of form-fitting or bonding methods such as, for example, crimping, welding, soldering, etc. It is also known to weld the coil in a bore extending through the sleeve. According to a further known connection type—preferably for non-weldable material combinations—the coil end is connected between two sleeves, by way of crimping, for example. The structure comprises a lower sleeve (rigid), contact wires located there between, and a crimping sleeve over it, which is plastically deformed to achieve a form-fit connection and, therefore, an electrical contact. This connection principle also functions with individual wires or cords. In this case, a coil is not located between the sleeves and, instead, radially or axially incoming wires or cords, which extend out of the coil connection of the catheter body, are folded and/or deformed to fit. Likewise, it is possible to insert these individual wires or cords into bores or sleeves for contacting, and to connect them in a bonded or form-fit manner (e.g., by welding or crimping).

The usability of these usual techniques for the connection of coil wires is limited in many regards, in particular with regard to the connection of the individual coil wires of coradial multiple coils at axially extending contact elements of plugs.

Proceeding from the problems of the prior art mentioned above, an objective of the present invention is to improve a conductive coil arrangement of the initially stated type in such a way that a structurally simple, universally applicable connection to contact elements of highly diverse types is made possible.

The present invention is directed toward overcoming one or more of the above-identified problems.

SUMMARY

A problem is solved according to a rough, basic concept in that the at least one individual coil wire of the multipolar conductive coil, which is to be contacted, is routed outwardly out of the wire interconnection of the conductive coil using a radial directional component, and the remainder of the conductive coil is routed further centrally axially through the contact zone.

Due to this design according to the present invention, a coradial coil is therefore transformed into radially offset individual coil wires which can then be better contacted. This separation is possible for an arbitrary number of conductors from the multipolar interconnection of coradial conductive coils.

According to a preferred embodiment of the present invention, the conductive coil, which is routed centrally axially further through the contact zone, is an individual coil wire, wherein the remaining, radially outwardly extending individual coil wires of the conductive coil are each in the form of individual contact coils which are disposed axially parallel and are preferably distributed equidistantly around the periphery. The latter can also have a smaller outer diameter relative to the outer diameter of the conductive coil, in a preferred manner.

The preferred embodiments noted above have an advantage that the typical properties of a coil, such as, for example, elasticity and insensitivity to fluctuations in bending stress, can be retained in a short installation space. By way of the reduction of the outwardly extending individual contact coils, the total outer diameter of the conductive coil arrangement can be reduced significantly in the region of the contact zones.

According to a development of the present invention related to the outwardly extending individual coils, contact pins inserted coaxially therein are provided as contact elements for the electrical connection of the particular individual coil wires. Since the contact pins are then positioned in the axially parallel direction, they can be easily coupled to cooperating contact elements of a connecting plug for the conductive coil arrangement.

The above-mentioned basic concept of the conductive coil arrangement according to the present invention can also be developed further, according to an alternative embodiment, in such a way that the conductive coil routed centrally axially through the contact zone comprises an individual coil wire, although, in deviation from the above-mentioned variant, the remaining individual coil wires of the conductive coil are disposed with the ends thereof projecting radially, each being connected to a contact element. Contact blocks or contact sleeves can be used for the latter. In association with contact blocks, the ends of the individual coil wires can each be inserted into respective connection bores or contact blocks in the radial direction or offset in the peripheral direction, where they are preferably secured by way of, for example, crimping, welding and/or soldering. When contact sleeves are used, contacting can take place by way of wall slots in the sleeve walls by inserting the ends of the wires therein the radial direction and securing them using typical contact fixing techniques. This measure is a structurally, particularly simple, reliable, and extremely compact variant for the separation of coil wires of the coradial conductive coil and the contacting thereof.

According to a further development of the subject matter of the present invention, the contact elements, such as the individual coil wires, contact blocks and/or sleeves, are distributed equidistantly around the circumference of the conductive coil arrangement in a common axial position which therefore overlaps at least partially. This arrangement permits a space-saving electrical connection of the conductive coil across a short axial length and a small diameter since the individual coil wires are contacted in the same axial plane region.

Further preferred embodiments of the present invention relate to the connection of the conductive coil arrangement to further-extending connection elements, such as plugs. For example, a so-called terminal block is provided in the contact zone, in or at which the contact elements of the individual coil wires are secured. This terminal block is a defined transition piece from the conductive coil arrangement to a multipolar plug connection element, wherein the contact elements of the individual coil wires secured in the terminal block are disposed in the plug connection element in accordance with the positions of the contact poles. The contacting of the individual coil wires of the conductive coil therefore takes place in a particularly efficient manner, since the contact elements can be positioned in accordance with the requirements of the particular plug connection unit. Alternatively, additional electrical contact elements, which are connected to the contact members of the individual coil wires, can also be disposed in the terminal block. These contact elements are then coupled to the particular plug element in an electrode catheter arrangement.

The various concepts of a conductive coil arrangement explained above can be implemented advantageously in an electrode catheter arrangement, the basic configuration of which comprises an elongated, tube-type catheter body. With the aid of the conductive coil arrangement according to the present invention, by using a corresponding terminal block, a plug which is known per se, such as, for example, a stated DF4/IS4 plug having axially disposed contacts, can be connected and, therefore electrically connected, to individual coil wires incoming radially out of the interconnection of the conductive coil. The plug element can therefore be multipolar in design, preferably having at least four poles. The coradial conductive coil can then comprise individual coil wires in an appropriate number, preferably four, interwoven in a coradial manner.

According to a particularly preferred embodiment, the conductive coil and the terminal block can undergo final assembly as a prefabricated module with the plug element.

The plug and the incoming electrical leads can therefore withstand tensile forces and can be interconnected electrically and mechanically in a manner that is insensitive to fluctuating bending stress. This takes place in minimal installation space, wherein an individual or multiple coil wire can also be guided centrally axially through the contact zone. The terminal block can therefore serve simultaneously with the central guide opening, which is also provided, to route a mandrel or guide wire, which are used as an implantation aid in the implantation of the electrode catheter.

In summary, the present invention and the preferred variants thereof provide a large number of advantages over the prior art, some of which are listed below as a summary:

The basic use of the coradial coil technique over cords avoids the problem of damage caused by forces and relative motions, in particular in the connection region at a plug.

Coil wires have better fluctuating bending stress properties than cords, and are better able to withstand tensile forces. It is therefore possible to avoid complex, coiled transfer pieces for relieving the tensile load on the cords.

Compared to cords, a conductive coil has better stability against radially acting forces, such as, for example, pinching at the catheter head.

Contact transfer within a very small installation space, as defined by the DF4/IS4 plug standard, for example, can therefore be achieved between a plug element and the conductive coil arrangement.

A type of modular system can be constructed in that the conductive coil arrangement having a corresponding terminal block forms a module that can be combined with a corresponding plug element as another module.

Further features, aspects, objects, advantages, and possible applications of the present invention will become apparent from a study of the exemplary embodiments and examples described below, in combination with the figures, and the appended claims.

DESCRIPTION OF THE DRAWINGS

Further features, details, and advantages of the present invention will become apparent from the description of exemplary embodiments, which follows, and with reference to the attached drawings. The figures show.

DETAILED DESCRIPTION

Figure 1:
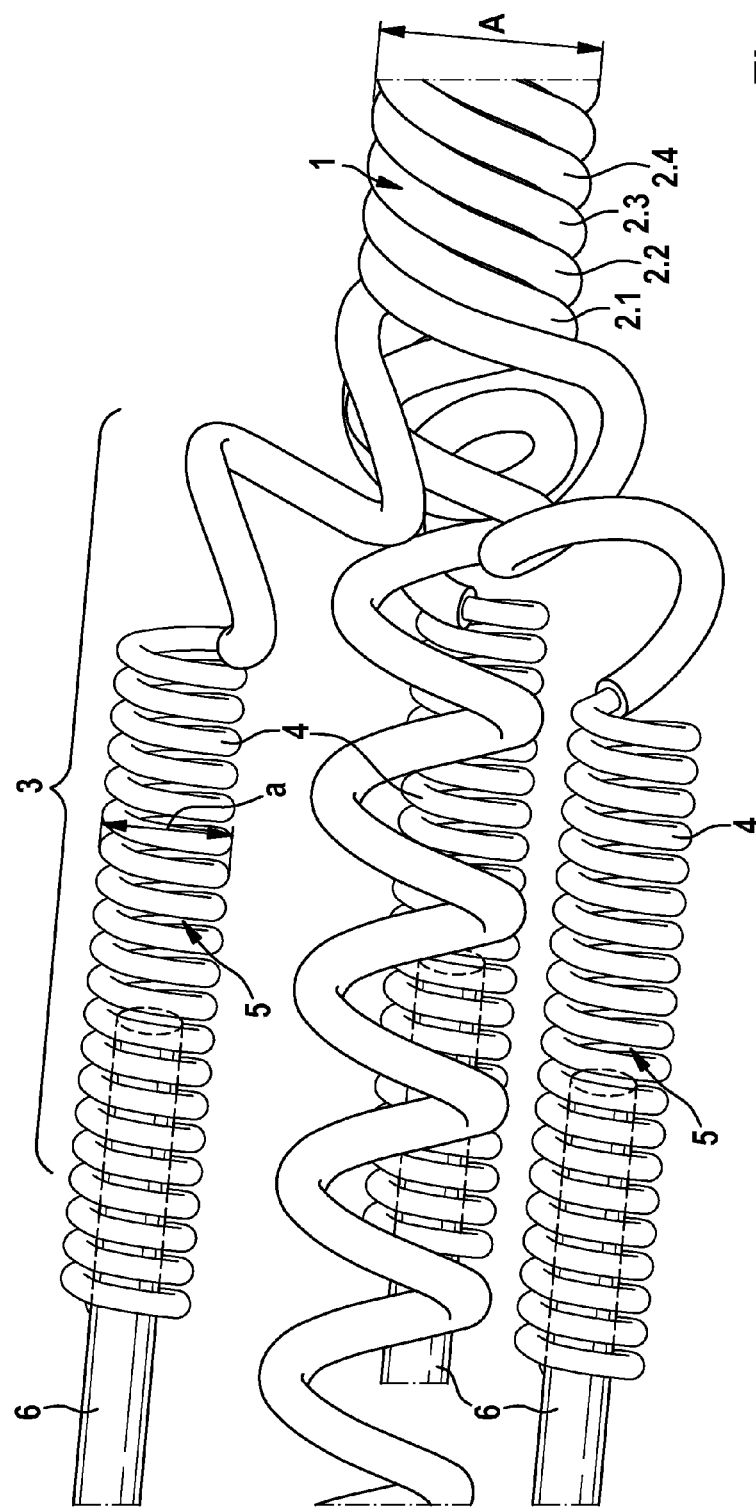
FIG. 1 shows a perspective view of a conductive coil arrangement in a first embodiment.

The conductive coil arrangement shown in FIG. 1 comprises a four-poled, coradial conductive coil 1 in which the four individual coil wires 2.1 to 2.4 are interwoven coradially as a unit, i.e., in the manner of a four-turn thread. The conductive coil 1 terminates in a contact zone, labelled in entirety with reference number 3, in which the individual coil wires 2.1 to 2.4 are connected to corresponding contact elements in a manner to be explained in greater detail hereafter.

In the contact zone 3, one individual coil wire 2.1 is routed further centrally axially through the contact zone 3 without the pitch of the coil winding or the diameter thereof being changed. The remaining three individual coil wires 2.2 to 2.4 are released from the coil interconnection and are routed outwardly with equal offset of 120° in the peripheral direction at a slant relative to one another, i.e., with a radial directional component and an axial directional component. The stripped ends 4 of the individual coil wires 2.1 to 2.4 are wound, as individual contact coils, with a diameter a which is markedly smaller than the outer diameter A of the conductive coil arrangement, to form a contact coil 5, all being oriented in the axially parallel direction. As contact elements for the electrical contacting of the individual coil wires 2.2 to 2.4, coaxial contact pins 6 are inserted and mechanically fixed into the contact coils 5 thereof. The latter can be achieved in a structurally simple manner by the spring force of the contact coils 5 and a corresponding oversize of the contact pin 6 relative to the inner diameter of the contact coils 5. An additional fixation with the aid of a soldering or welding point or the like, for example, can also be provided for safety reasons. The contact pins 6 can be connected in the axial direction using the contact elements, which are not depicted in greater detail herein, of a plug element, for example, and the conductive coil arrangement can therefore be connected to a plug element.

Figure 2:
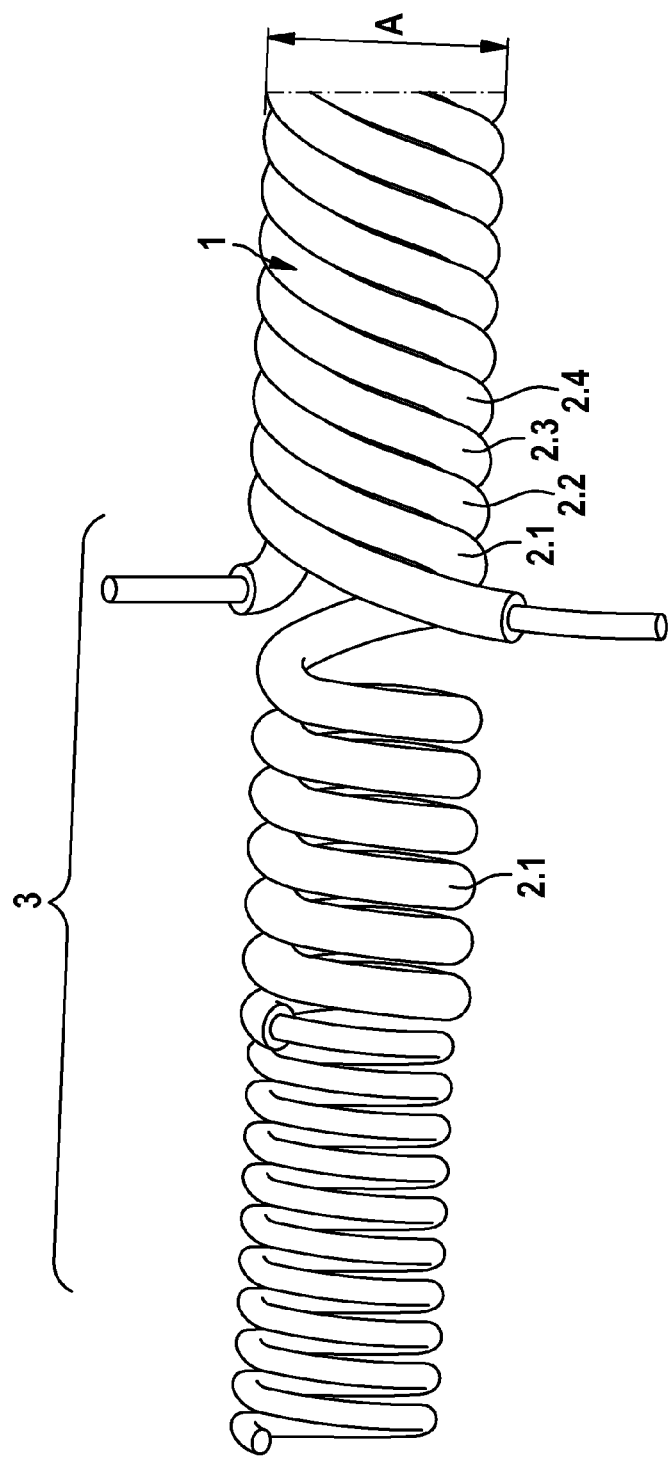
FIGS. 2-4 show perspective views of a conductive coil arrangement having a plug element coupled thereto, in a second embodiment in basic degrees of cut-out.
Figure 3:
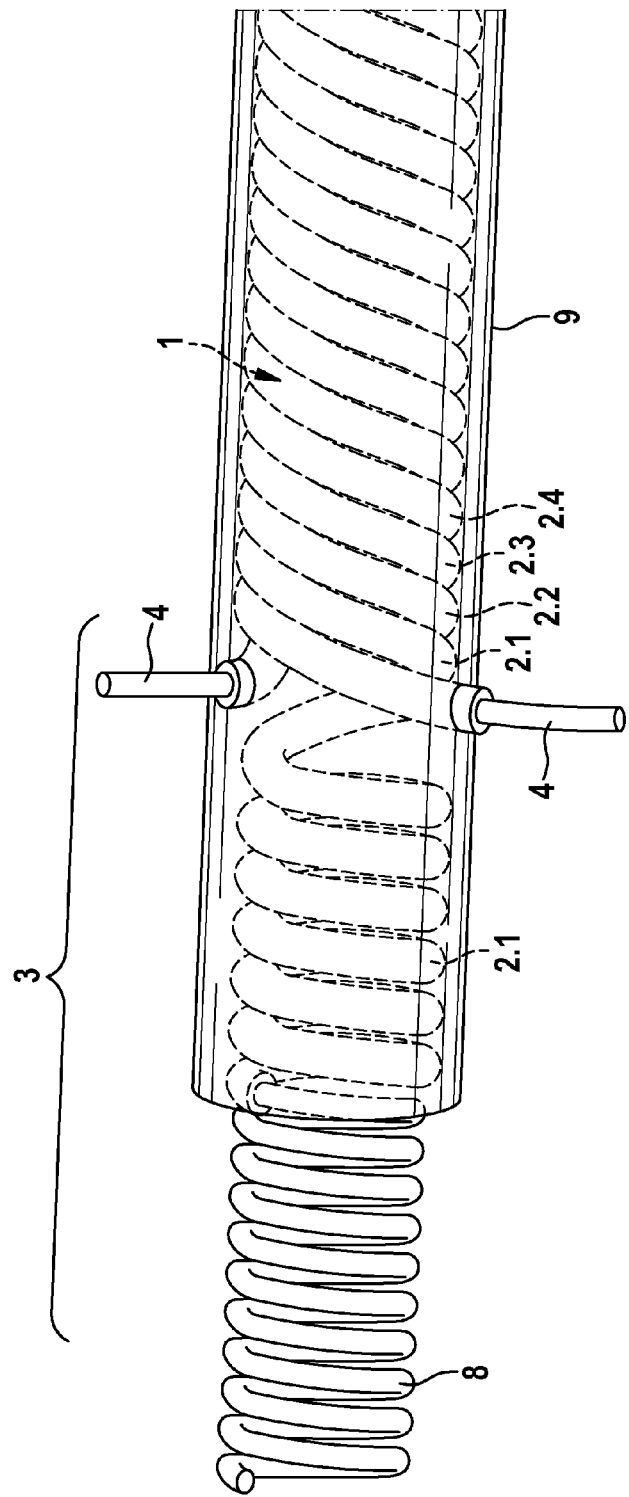
Figure 4:
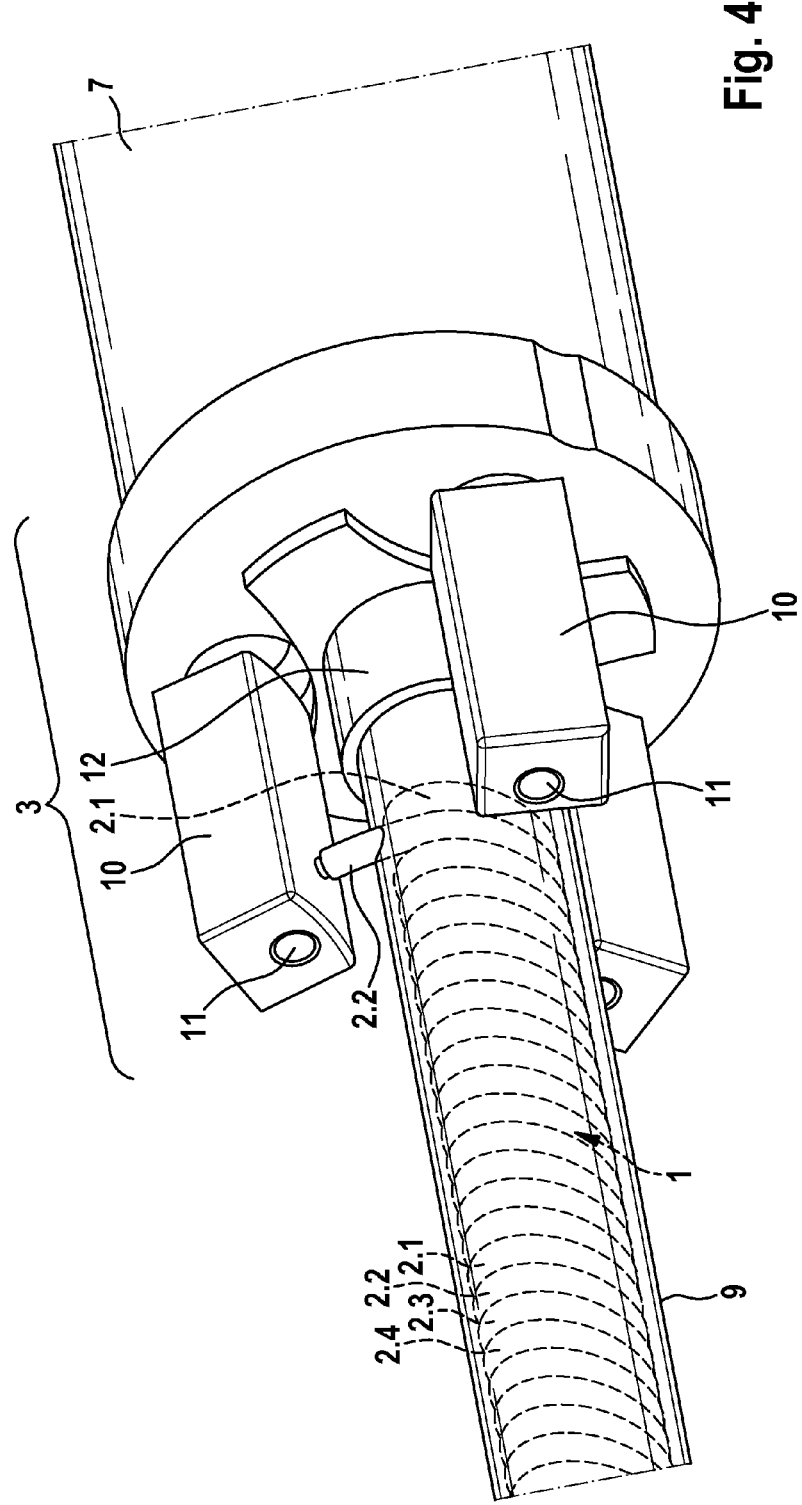

FIGS. 2-4 show, in various basic degrees of cut-out, a further embodiment of a conductive coil arrangement in which the conductive coil 1 is connected to a plug element 7. As shown clearly in FIG. 2, the one individual coil wire 2.1 is guided further coaxially and, although, in contrast to the embodiment according to FIG. 1, is wound as a unit in the further section and is stripped at the end 8 thereof.

The remaining individual coil wires 2.2 to 2.4 are shortened and moved away from the conductive coil 1, projecting outwardly in the radial direction. Due to the perspective view, only the two ends 4 of the individual coil wires 2.3 and 2.4 are visible in FIGS. 2-3.

The conductive coil 1 widened in this manner is then provided with an insulating tube 9 which terminates before the stripped end 8 of the central individual coil wire 2.1. The stripped ends 4 of the remaining individual coil wires 2.2 to 2.4 project in the radial direction outwardly through the insulating tube 9.

As shown in FIG. 4, elongated, cuboid contact blocks 10 are inserted onto these stripped ends 4, and are mechanically and electrically connected to the ends 4 using typical contact connection measures of joining technology, such as, for example, crimping, welding, soldering, and the like. The contact blocks 10 comprise bores 11 which extend axially parallel, and into which contact pins of the plug element 7 are inserted and can be connected mechanically and electrically to the contact blocks 10 by way of the usual joining methods mentioned above.

The central individual coil wire 2.1 is inserted into a corresponding receptacle 12 of the plug element 7 and is likewise connected there mechanically and electrically to a central contact pole of the plug element 7 in a suitable manner.

Due to the flexibility of the conductive coil, the transition to the plug element 7 shown can be achieved in a manner that transfers tensile force, is insensitive to fluctuating bending stress, and is compact.

Figure 5:
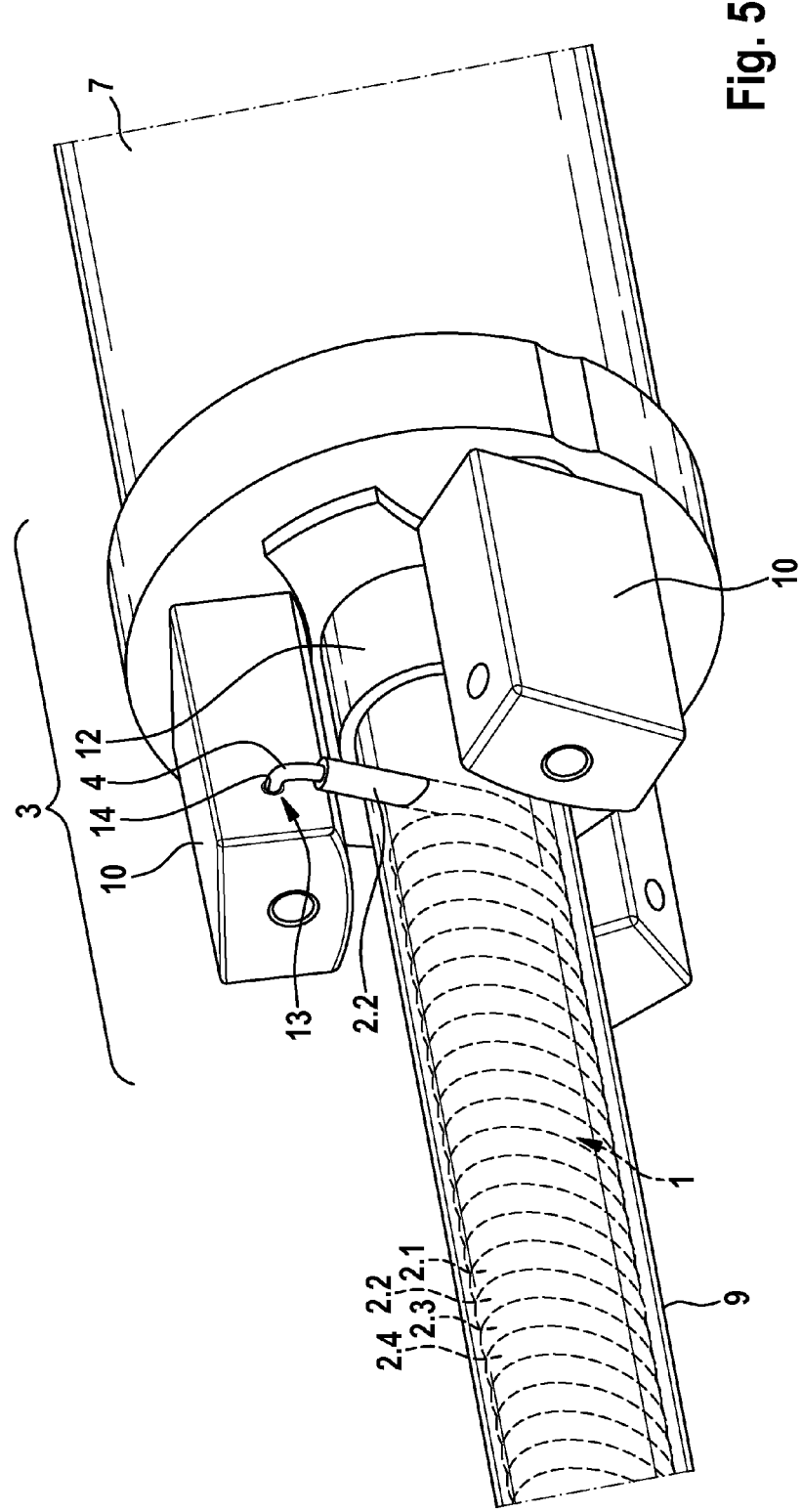
FIGS. 5-6 show a perspective view of a conductive coil arrangement having a connected plug element in a third and fourth embodiment.

FIG. 5 shows a detailed variant of the embodiment according to FIG. 4. In this case, the radially projecting ends 4 of the individual coil wires 2.2 to 2.4 are inserted laterally with an offset 13 in the peripheral direction into a corresponding receiving hole 14 in the contact blocks 10 and are fixed therein. For the rest, reference is made to the description of FIG. 4 with regard to the contact blocks 10 and the connection thereto to the plug element 7.

Figure 6:
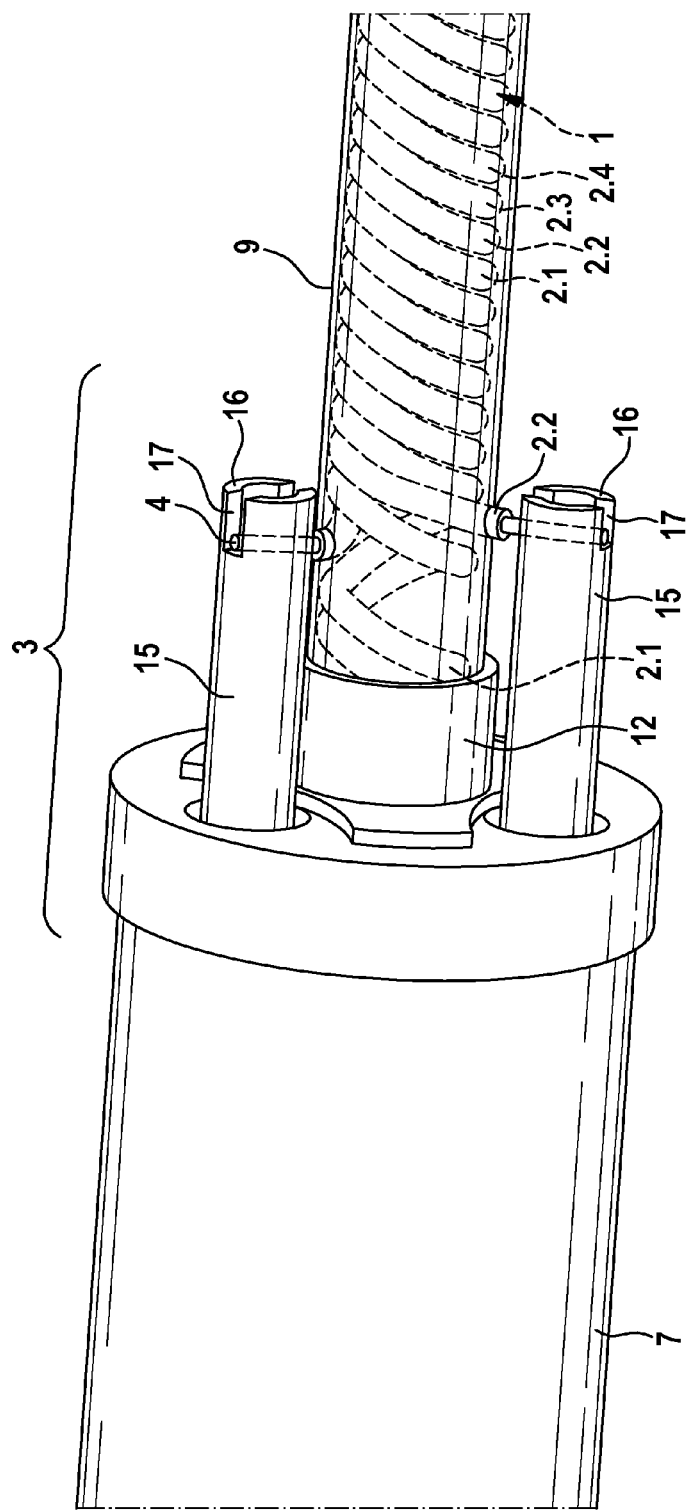

A further alternative embodiment of the connection of a plug element 7 to a conductive coil 1 is shown in FIG. 6. The conductive coil 1 comprises four individual coil wires 2.1 to 2.4 which are prepared in a manner analogous to the intermediate production steps shown in FIGS. 2 and 3. Reference can be made to the description therein this regard.

In this embodiment according to FIG. 6, the radially projecting ends 4 of the individual coil wires 2.2 to 2.4 are fastened in contact sleeves 15 which, in turn, are disposed axially parallel equidistantly in the circumferential direction. The connection between the stripped ends 4 of the individual coil wires 2.2 to 2.4 with the contact sleeves 15 takes place by way of slots 17 formed in the end-face edges 16 of the contact sleeves 15 in a longitudinal axial plane, in which the ends 4 can be fastened once more by way of the joining methods mentioned above.

The contact sleeves 15 are electrically and mechanically connected to the corresponding contact poles of the plug element 7. In the same manner, the central individual coil wire 2.1 is coupled by way of a receptacle 12 to the plug element 7 and is connected to a central pole thereof.

Figure 7:
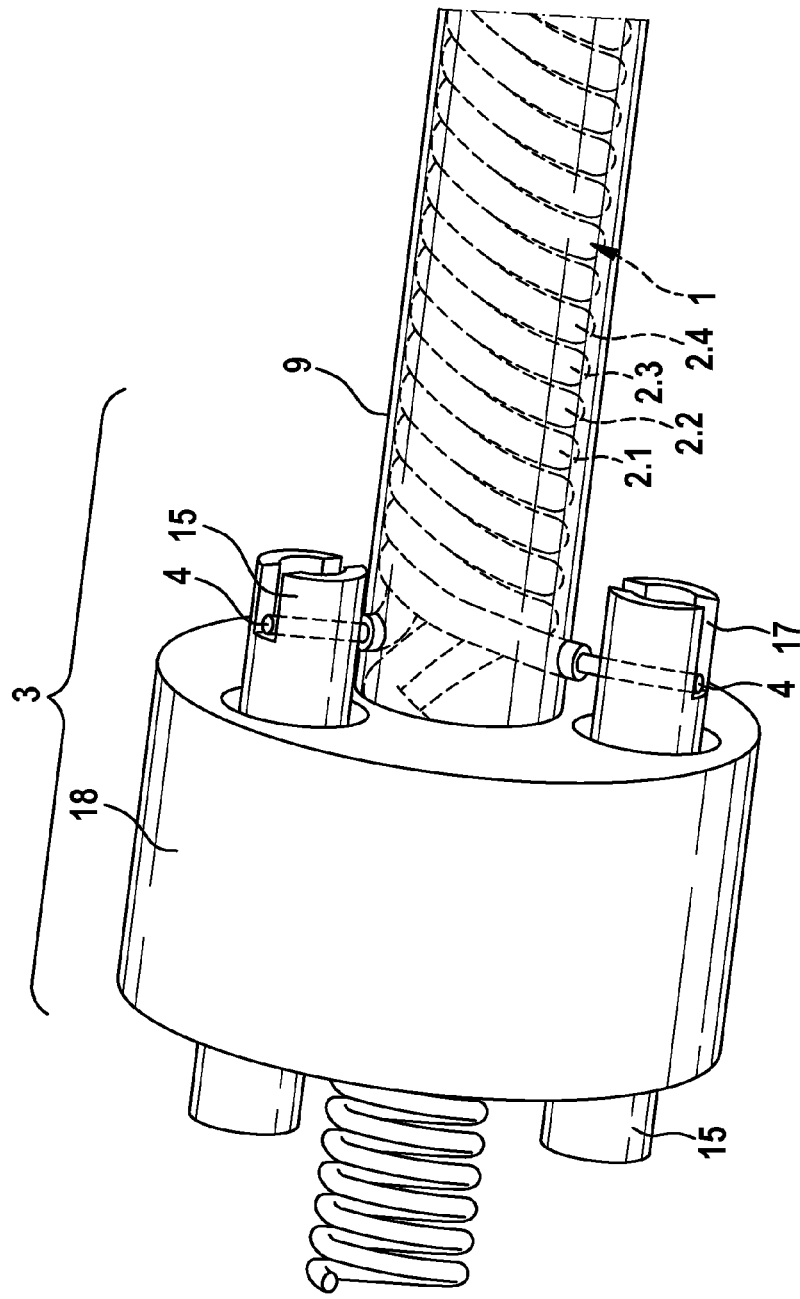
FIG. 7 shows a perspective view of a conductive coil arrangement comprising a terminal block.

FIG. 7 shows an exemplary embodiment of a conductive coil arrangement, in which the contact elements in the form of contact sleeves 15, which are connected as in FIG. 6, of the radially outwardly extending individual coil wires 2.2 to 2.4 and the central receptacle 12 for the central individual coil wire 2.1 are fixed in a terminal block 18. The latter is made of an insulating material and corresponds by way of the cylindrical shape thereof—as shown herein—in the outer diameter to a plug element 7 via which the terminal block 18 is coupled to the plug element 7 mechanically and, via the contact elements, electrically to the plug element 7, as shown in FIG. 9 and as explained in greater detail below.

Figure 8:
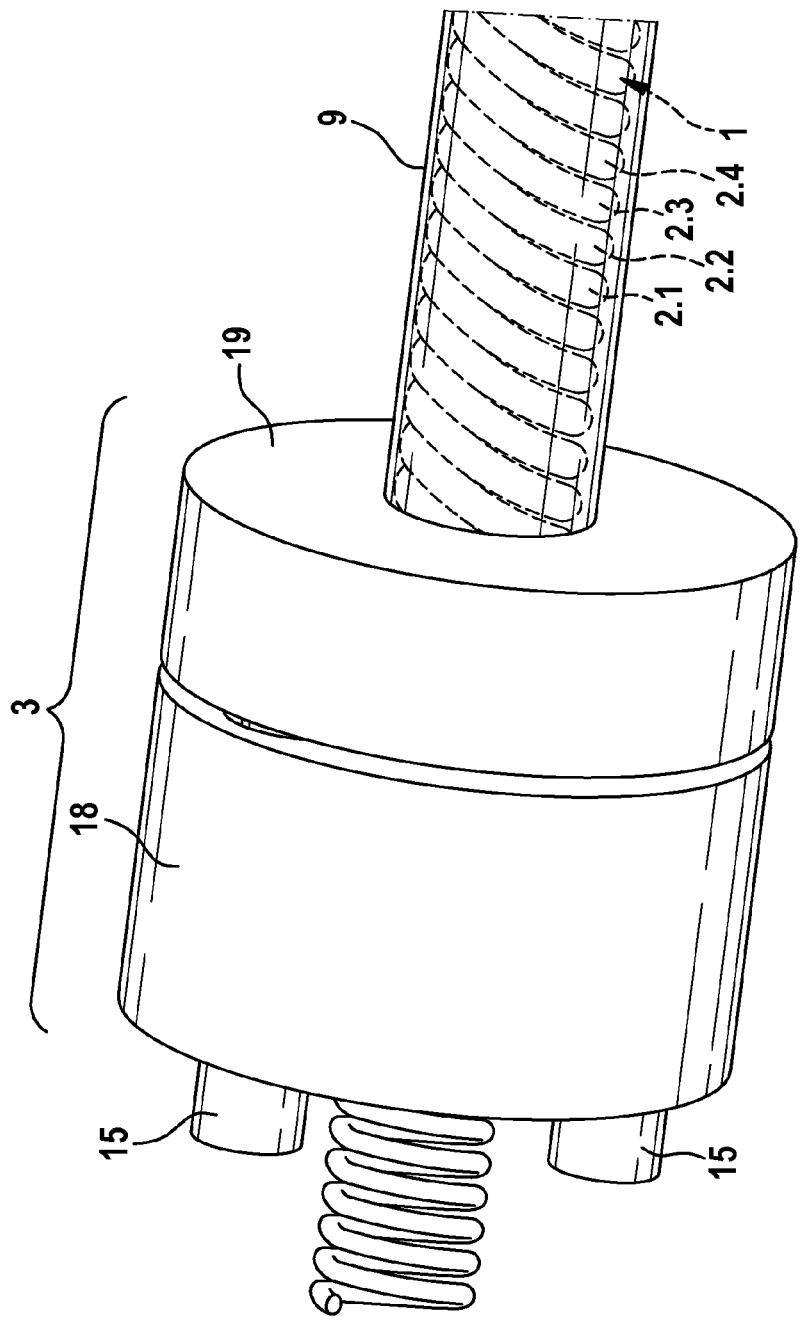
FIG. 8 shows the arrangement according to FIG. 7, comprising a cover cap.

FIG. 8 shows the conductive coil 1 with terminal block 18 according to FIG. 7, wherein one more insulating cover cap 19 encloses the space in which the slots 17 in the contact sleeves 15 are disposed with the stripped ends 4 of the individual coil wires 2.2 to 2.4. These contact points are therefore mechanically protected and electrically insulated to the outside.

Figure 9:
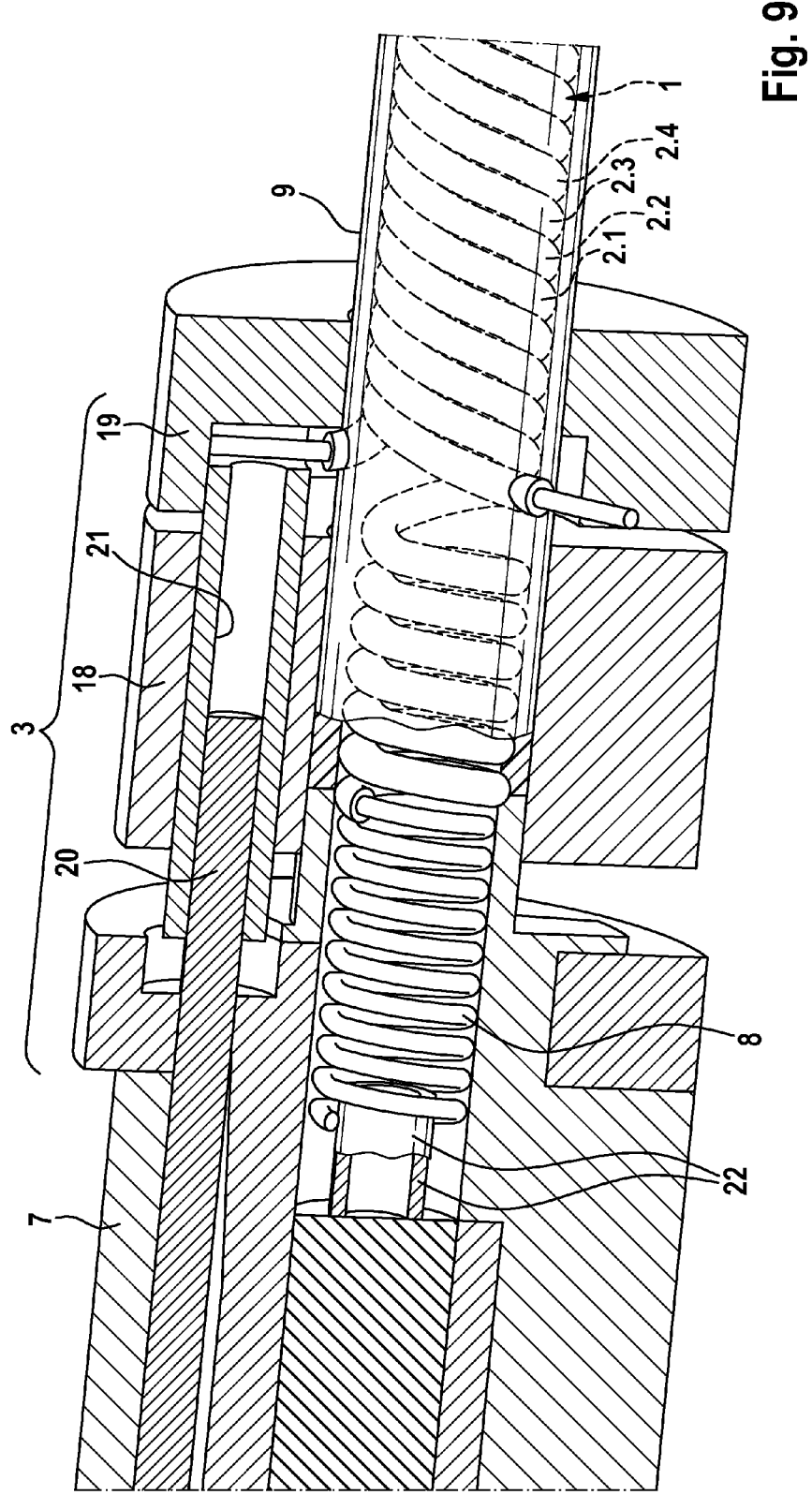
FIG. 9 shows an axial section of the arrangement according to FIG. 8, with plug element attached.

The above-mentioned embodiment illustrated in FIG. 9 shows the conductive coil arrangement comprising the conductive coil 1 and the terminal block 18 with the cover cap 19 in a configuration assembled together with the plug element 7. The plug element 7 comprises contact pins 20, which are aligned axially with the contact sleeves 15, for the particular plug pole, which are inserted into the inner opening 21 of the contact sleeves 15 and are mechanically and electrically connected therewith. The central individual coil wire 2.1 is mechanically and electrically connected by way of the stripped end thereof to the central contact pole 22. The overall result is a connection of the four-pole conductive coil 1 to a plug element having one central pole and three axially parallel contact poles 22 distributed equidistantly in the peripheral direction, only one of which is visible in FIG. 9, with the associated contact sleeve 15. It is furthermore pointed out that the terminal block is provided with a centrally continuous guide opening 24 for a guide wire or a mandrel as an implantation aid.

Figure 10:
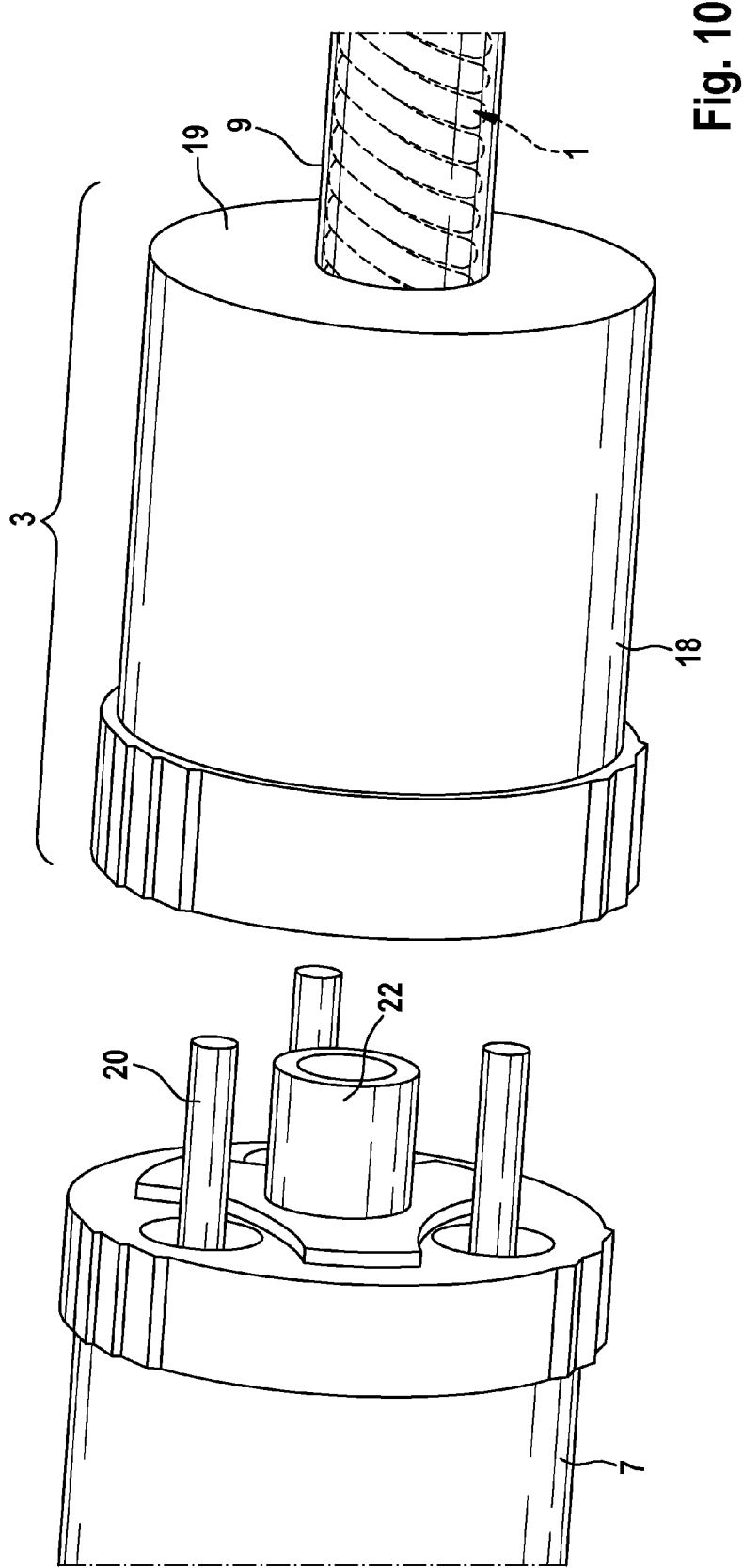
FIGS. 10-11 show perspective views of the arrangement according to FIG. 9, from two different viewing angles in the preassembled state.
Figure 11:
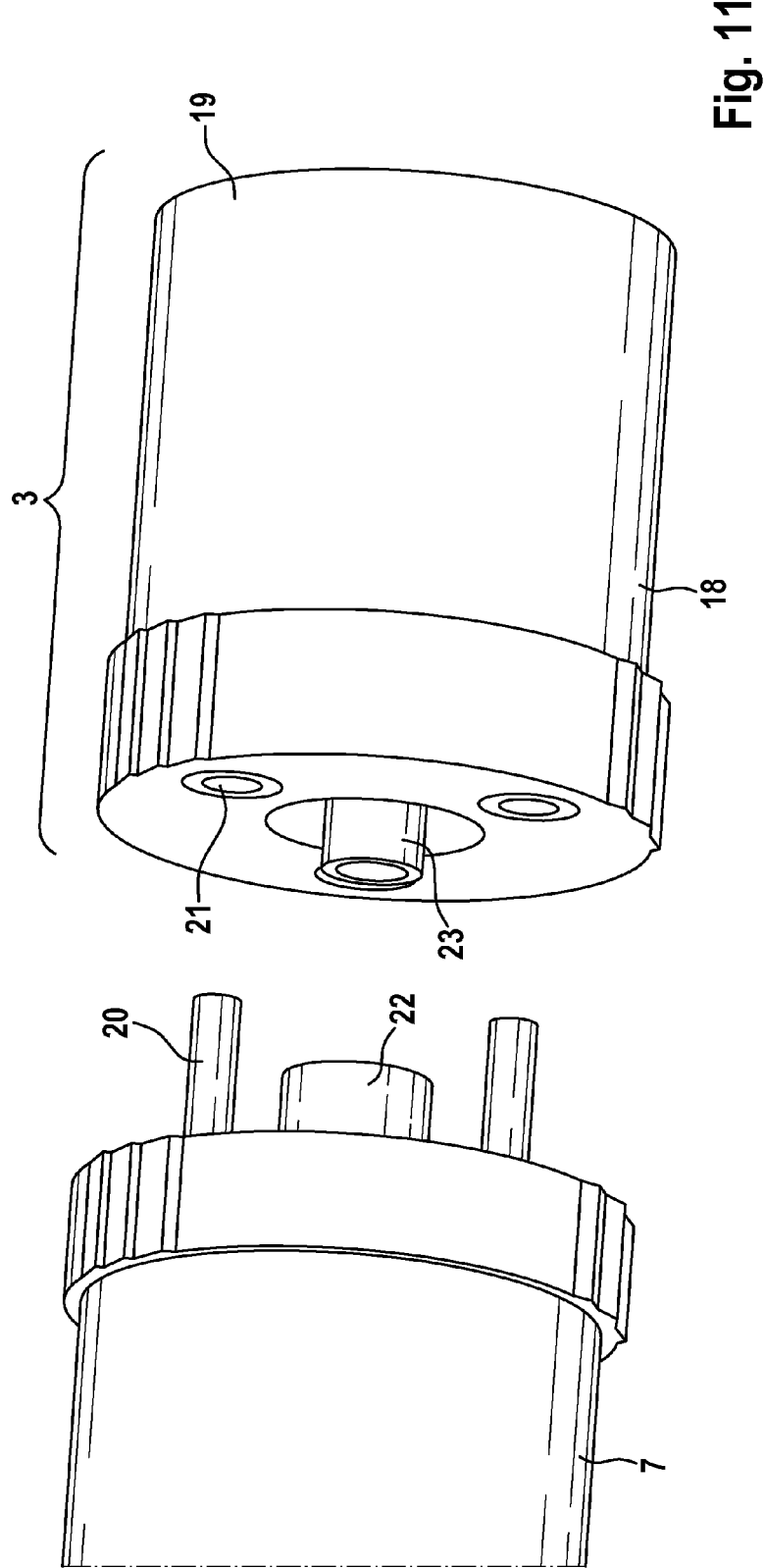

FIGS. 10-11 explicitly show that the conductive coil 1 can be preassembled with a corresponding insulating tube 9 and a terminal block 18 as a modular assembly, just like the plug element 7 with three contact pins 20 thereof and the central contact pole 22. The final assembly takes place simply by inserting the plug element 7 into the terminal block 18 of the conductive coil 1 with mechanical and electrical connection to the contact sleeves 15.

One more variant is shown in FIG. 11 with regard to the contact connection between the central contact pole 22 of the plug element 7 and the central individual coil wire 2.1. The latter is provided with a contact pin 23 on the end 8 thereof, which can be connected to the contact pole 22 in a structurally particularly simple manner by way of mutual insertion.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. A conductive coil arrangement for electrode catheters for cardiac therapy, comprising:
    a multipolar conductive coil having a plurality of coradially interwoven, individual coil wires; and
    a contact zone in which at least one individual coil wire from the conductive coil is configured for connection to a contact element for electrical contacting,
    wherein the at least one individual coil wire to be contacted is routed outwardly out of the wire interconnection of the conductive coil with a radial direction component,
    wherein the remainder of the conductive coil is routed further centrally axially through the contact zone,
    wherein the conductive coil, which is routed further centrally axially through the contact zone, comprises an individual coil wire, and the remaining radially outwardly extending individual coil wires of the conductive coil are in the form of individual contact coils which are disposed axially parallel and are distributed equidistantly around the periphery, and
    wherein the individual coils have a smaller outer diameter (a) relative to the outer diameter (A) of the conductive coil.

2. A conductive coil arrangement for electrode catheters for cardiac therapy, comprising:
    a multipolar conductive coil having a plurality of coradially interwoven, individual coil wires; and
    a contact zone in which at least one individual coil wire from the conductive coil is configured for connection to a contact element for electrical contacting,
    wherein the at least one individual coil wire to be contacted is routed outwardly out of the wire interconnection of the conductive coil with a radial direction component,
    wherein the remainder of the conductive coil is routed further centrally axially through the contact zone,
    wherein the conductive coil, which is routed further centrally axially through the contact zone, comprises an individual coil wire, and the remaining radially outwardly extending individual coil wires of the conductive coil are in the form of individual contact coils which are disposed axially parallel and are distributed equidistantly around the periphery, and
    wherein coaxial contact pins are configured for insertion into the individual coils, as the contact element for the electrical connection thereof.

3. The conductive coil arrangement according to claim 1, wherein the conductive coil, which is routed further centrally axially through the contact zone, comprises an individual coil wire, and the remaining individual coil wires of the conductive coil are arranged in a radially projecting manner by way of the ends thereof, each being connected to a respective contact element.

4. A conductive coil arrangement for electrode catheters for cardiac therapy, comprising:
    a multipolar conductive coil having a plurality of coradially interwoven, individual coil wires; and
    a contact zone in which at least one individual coil wire from the conductive coil is configured for connection to a contact element for electrical contacting,
    wherein the at least one individual coil wire to be contacted is routed outwardly out of the wire interconnection of the conductive coil with a radial direction component,
    wherein the remainder of the conductive coil is routed further centrally axially through the contact zone,
    wherein the conductive coil, which is routed further centrally axially through the contact zone, comprises an individual coil wire, and the remaining individual coil wires of the conductive coil are arranged in a radially projecting manner by way of the ends thereof, each being connected to a respective contact element, and
    wherein the contact elements are each formed by contact blocks or contact sleeves.

5. The conductive coil arrangement according to claim 4, wherein the ends of the individual coil wires are inserted into connection bores of the contact blocks in the radial direction, and are secured by way of crimping, welding and/or soldering.

6. The conductive coil arrangement according to claim 4, wherein the ends of the individual coil wires are inserted into connection bores of the contact blocks offset in the peripheral direction, and are secured by way of crimping, welding and/or soldering.

7. The conductive coil arrangement according to claim 4, wherein the ends of the individual coil wires are inserted into wall slots of the contact sleeves in the radial direction and are secured by way of crimping, welding and/or soldering.

8. A conductive coil arrangement for electrode catheters for cardiac therapy, comprising:
    a multipolar conductive coil having a plurality of coradially interwoven, individual coil wires; and
    a contact zone in which at least one individual coil wire from the conductive coil is configured for connection to a contact element for electrical contacting,
    wherein the at least one individual coil wire to be contacted is routed outwardly out of the wire interconnection of the conductive coil with a radial direction component,
    wherein the remainder of the conductive coil is routed further centrally axially through the contact zone, and
    wherein the contact elements are distributed equidistantly around the circumference of the conductive coil arrangement, and are disposed in a common axial position.

9. A conductive coil arrangement for electrode catheters for cardiac therapy, comprising:
    a multipolar conductive coil having a plurality of coradially interwoven, individual coil wires; and
    a contact zone in which at least one individual coil wire from the conductive coil is configured for connection to a contact element for electrical contacting,
    wherein the at least one individual coil wire to be contacted is routed outwardly out of the wire interconnection of the conductive coil with a radial direction component,
    wherein the remainder of the conductive coil is routed further centrally axially through the contact zone, and
    wherein a terminal block is provided in the contact zone, in or at which the contact elements of the individual coil wires are secured.

10. The conductive coil arrangement according to claim 9, wherein electrical contact elements are disposed in the terminal block, which are connected to the contact elements of the individual coil wires or are formed thereby, and to a plug element in an electrode catheter arrangement.

11. An electrode catheter arrangement for cardiac therapy, comprising:

an elongated, tube-type catheter body, comprising:

a conductive coil arrangement coupled to a terminal block, the conductive coil arrangement comprising:

a multipolar conductive coil having a plurality of coradially interwoven, individual coil wires; and a contact zone in which at least one individual coil wire from the conductive coil is configured for connection to a contact element for electrical contacting, wherein the at least one individual coil wire to be contacted is routed outwardly out of the wire interconnection of the conductive coil with a radial direction component, and wherein the remainder of the conductive coil is routed further centrally axially through the contact zone; and a plug element, which is coupled to the terminal block, wherein the plug element is at least four-poled, and the coradial conductive coil comprises at least four individual coil wires interwoven in a coradial manner.

12. The electrode catheter arrangement according to claim 11, wherein the conductive coil and the terminal block are configured to undergo final assembly as a prefabricated module with the plug element.

13. The electrode catheter arrangement according to claim 11, wherein the terminal block is provided with a guide opening for an implantation aid in the region of the centrally axially routed conductive coil.

* * * * *